US00PP23128P2

(12) United States Plant Patent
Dirr

(10) Patent No.: US PP23,128 P2
(45) Date of Patent: Oct. 23, 2012

(54) ***DISTYLIUM* PLANT NAMED 'VINTAGE JADE'**

(50) Latin Name: ***Distylium* sp. hybrid**
Varietal Denomination: Vintage Jade

(75) Inventor: Michael A. Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/068,237

(22) Filed: May 6, 2011

(51) Int. Cl.
*A01H 5/00* (2006.01)

(52) U.S. Cl. ..... Plt./226
(58) Field of Classification Search ..... Plt./226
See application file for complete search history.

(56) References Cited

OTHER PUBLICATIONS

Plant Introductions, Inc.—promotional page from Plant Introductions website showing color pictures of *Distylium* Hybrids (*Distylium* hybrid 16 is *Distylium* plant named Vintage Jade), downloaded May 5, 2011.

*Primary Examiner* — Annette Para
(74) *Attorney, Agent, or Firm* — Greenlee Sullivan P.C.

(57) ABSTRACT

A new and distinct cultivar of *Distylium* plant named 'Vintage Jade', characterized by its compact, layered, mounding and spreading growth habit, light green new growth, dark green mature foliage, and reddish maroon flowers.

3 Drawing Sheets

Genus and species of plant claimed: *Distylium* sp. hybrid. Variety denomination: 'Vintage Jade'.

BACKGROUND OF THE INVENTION

The present invention relates to a new and distinct cultivar of *Distylium* plant, botanically known as *Distylium* sp. hybrid, a member of the Hamamelidaceae, and hereinafter referred to by the cultivar name 'Vintage Jade'.

'Vintage Jade' originated as an open-pollinated seedling from seed collected from a *Distylium* sp. hybrid (*Distylium myricoides*×*D. racemosum*) growing in Watkinsville, Ga. 'Vintage Jade' was selected in the summer of 2006 by the inventor in a cultivated environment in Dearing, Ga.

Asexual reproduction of 'Vintage Jade' by stem cuttings since 2006 has shown that all the unique features of 'Vintage Jade', as herein described, are stable and reproduced true-to-type through successive generations of such asexual propagation.

SUMMARY OF THE INVENTION

Plants of the new cultivar 'Vintage Jade' have not been observed under all possible environmental conditions. The phenotype may vary somewhat with changes in light, temperature, soil and rainfall without, however, any variance in genotype.

The following traits have been repeatedly observed and are determined to be unique characteristics of 'Vintage Jade'. These characteristics in combination distinguish 'Vintage Jade' as a new and distinct cultivar: 1. Compact, layered, mounding and spreading growth habit; 3. Light green new growth; 3. Dark green mature foliage; and 4. Reddish maroon flowers.

Plants of 'Vintage Jade' differ from plants of the parent, *Distylium* sp. hybrid, primarily in growth habit, foliage color, and cold hardiness, as plants of 'Vintage Jade' have a smaller, more compact, mounding and spreading growth habit, large lustrous dark green mature foliage, and increased cold hardiness, whereas plants of the parent have a larger, less compact, upright, spreading growth habit, smaller medium green foliage, and are less cold hardy.

Plants of the new *Distylium* 'Vintage Jade' can be compared to plants of the cultivar 'PIIDIST-I' (U.S. Plant patent application Ser. No. 13/068,262), which is a sibling that originated from the same open-pollination. 'Vintage Jade' has a has a compact, layered, mounding and spreading growth habit, light green new growth, dark green mature foliage, and reddish maroon flowers, whereas 'PIIDIST-I' has a compact, upright-spreading growth habit, yellow-green new growth, dark green mature foliage, and reddish purple flowers.

Plants of the new *Distylium* 'Vintage Jade' can be compared to plants of the cultivar 'PIIDIST-II' (U.S. Plant patent application Ser. No. 13/068,251), which is a sibling that originated from the same open-pollination. 'Vintage Jade' has a compact, layered, mounding and spreading growth habit, light green new growth, dark green mature foliage, and reddish maroon flowers, whereas 'PIIDIST-II' has a compact, spreading growth habit, maroon-purple new growth, dark blue-green mature foliage, and reddish maroon flowers.

BRIEF DESCRIPTION OF THE DRAWINGS

The accompanying color photographs illustrate the flower and foliage characteristics and the overall appearance of 'Vintage Jade', showing the colors as true as it is reasonably possible to obtain in color reproductions of this type. Colors in the photographs may differ slightly from the color values cited in the detailed botanical description which accurately describe the colors of 'Vintage Jade'.

DETAILED DESCRIPTION

Figure 1:
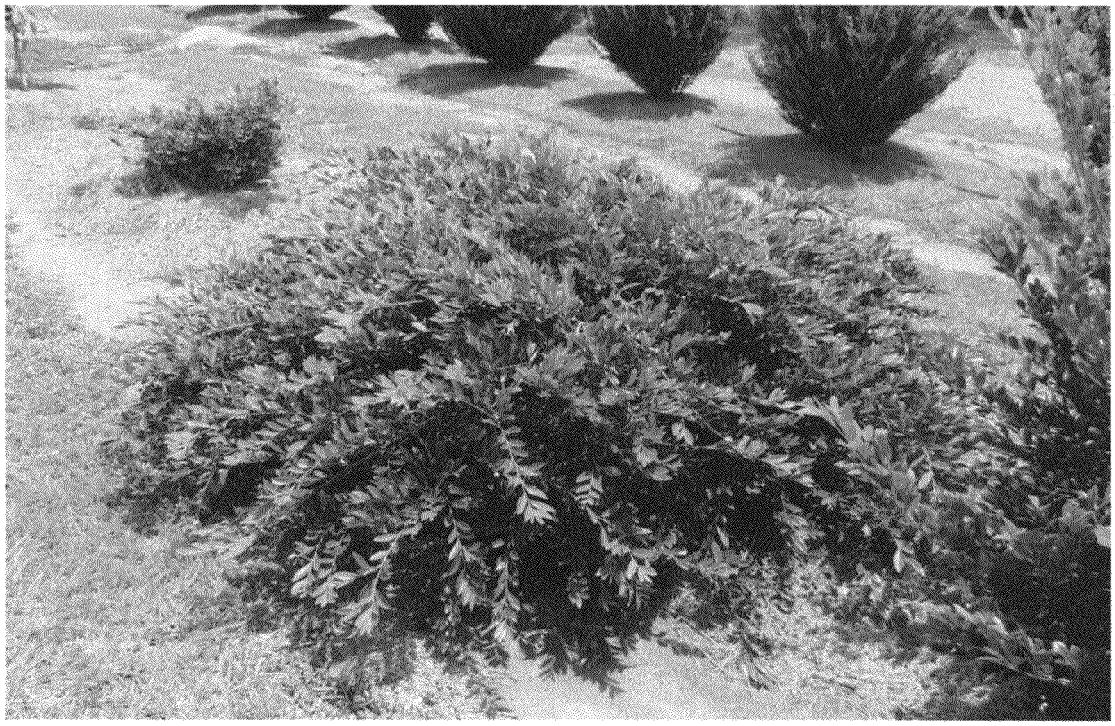
FIG. 1 illustrates the overall appearance and growth habit of 'Vintage Jade'.
Figure 2:
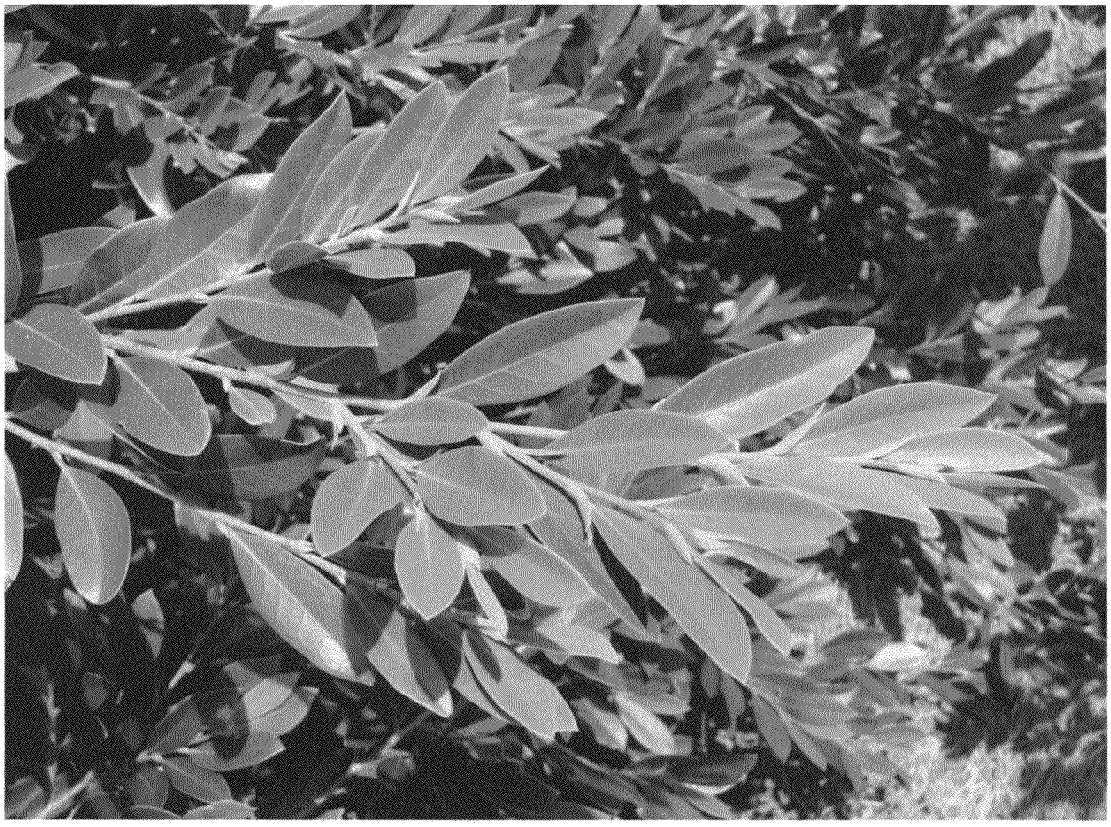
FIG. 2 illustrates a close-up view of the new growth and mature foliage of 'Vintage Jade'.
Figure 3:
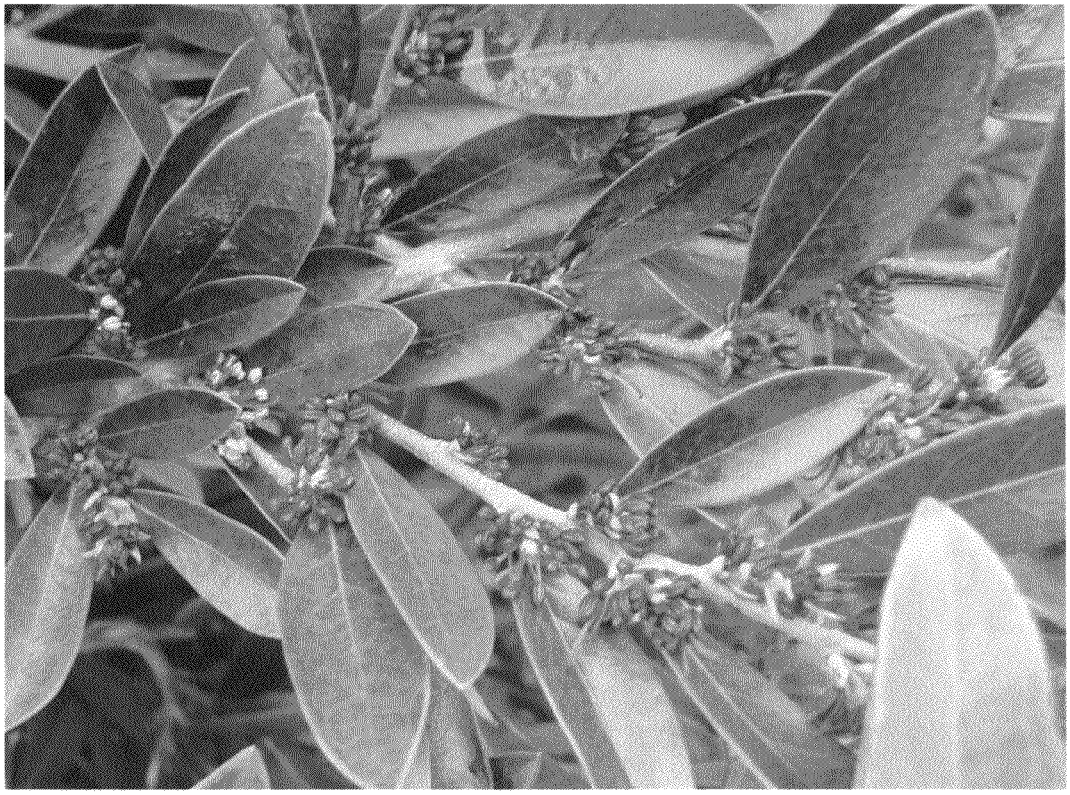
FIG. 3 illustrates a close-up view of the flowers of 'Vintage Jade'.

In the following description, color references are made to The Royal Horticultural Society Colour Chart, 2001 Edition, except where general terms of ordinary dictionary significance are used. Plants used for the description were approximately 3-years-old and were grown in 11.8 L containers under outdoor conditions in Watkinsville, Ga.

Botanical classification: *Distylium* sp. hybrid, cultivar 'Vintage Jade'.

Parentage: *Distylium* sp. hybrid.

Propagation: Stem cuttings.

Time to initiate roots in summer: About 3 to 4 weeks at 32° C.

Plant description: Broadleaf evergreen flowering shrub; multi-stemmed; compact, mounding and spreading growth habit. Freely branching; removal of the terminal bud enhances lateral branch development.

*Root description*.—Medium, well-branched.

*Plant size*.—The original plant, now about five-years-old in the ground, is about 81 cm high from the soil level to the top of the foliage and about 244 cm wide.

*First year stems*.—Having a diameter of about 2 mm. Shape: round. Fine pubescence. Few small lenticels about 1 mm in diameter and N199B in color.

*First year stem color*.—146A.

*Second year and older stems*.—Have a diameter of about 4 mm or more. Shape: round.

*Second year and older stem color*.—199B.

*Stem strength*.—Flexible when young, less flexible once mature.

*Internode length*.—About 1.4 cm.

*Trunk diameter*.—About 1.9 cm at the soil line. Color: 199A. Bark: does not exfoliate, covered with many lenticels about 1 mm in diameter and N199B in color.

Vegetative bud description:

*Arrangement*.—Alternate.

*Shape*.—Ovoid with fused, pubescent bud scales.

*Size*.—About 3 mm in length and about 2 mm in width.

*Color*.—199A.

Foliage description:

*Arrangement*.—Alternate, simple. Length: about 6.2 cm. Width: about 2.1 cm. Shape: Elliptical. Apex: Acute. Base: Cuneate. Margin: entire, occasionally undulating.

*Texture* (*upper and lower surfaces*).—Thick, leathery.

*Venation pattern*.—Pinnate. Venation color (upper and lower surfaces): midrib color is 147B and secondary vein color is 147A.

*Color of emerging foliage* (*upper surface*).—144A. Color of emerging foliage (lower surface): 144B. Color of mature foliage (upper surface): 147A. Color of mature foliage (lower surface): 146B.

*Petiole length*.—About 4 mm. Petiole diameter: about 1 mm. Fine pubescence 199B in color. Petiole color (upper and lower surfaces): 146A.

Flower description:

*Flower type and habit*.—Apetalous flowers with a pubescent, 5-parted calyx are borne on short racemes from the leaf axils. Natural flowering season: late winter, approximately January to February in Watkinsville, Ga. Individual flowers are showy for approximately 1 week and are self-cleaning.

*Flower size*.—About 1 cm in diameter and about 1.1 cm in height.

*Pedicels*.—About 2 mm in length. Peduncles: about 1.2 cm in length. Color: pedicels and peduncles 146C in color with pubescence 165A in color.

Stamens:

*Quantity/arrangement*.—7 to 10 per flower. Filament: about 3 mm in length, less than 1 mm in width, and 146D in color. Anthers: about 2 mm in length, about 1 mm in width, and 185A in color. Pollen: produced in moderate quantities and is 158D in color.

Pistils:

*Position*.—Superior. Size: about 1.1 mm in length and about 2 mm in width. Color: 146B. Stigma: 2 per pistil, about 6 mm in length, 178B in color. Style: 2 per flower, about 3 mm in length, and 146B in color. Ovary: two per flower, about 2 mm in diameter, about 2 mm in height, and 146B in color.

Fruit:

*Type/appearance*.—2-valved, beaked woody capsule containing 2 seeds, one per valve. Fruit size: the capsule is about 1.5 cm long and about 7 mm wide. Mature color: 200C. Seeds: oblong to elliptical in shape, about 5 mm in length, about 2 mm in width, and N200A in color.

Disease/pest resistance: Plants of the new *Distylium* grown in the nursery and garden have not been noted to be susceptible to pathogens or pests.

I claim:

1. A new and distinct *Distylium* plant named 'Vintage Jade', as illustrated and described herein.

* * * * *